United States Patent [19]

Bori

[11] Patent Number: 4,752,225

[45] Date of Patent: Jun. 21, 1988

[54] ENDODONTIC POST AND METHOD OF TREATMENT

[76] Inventor: Jacques Bori, 11 Rue Cognacq-Jay, Paris 75007, France

[21] Appl. No.: 914,818

[22] Filed: Oct. 3, 1986

[51] Int. Cl.⁴ .............................................. A61C 3/08
[52] U.S. Cl. .................................................. 433/221
[58] Field of Search ........................ 433/221, 220, 225

[56] References Cited

U.S. PATENT DOCUMENTS 4,515,565  5/1985  Winter-Moore .................... 433/221
4,600,391  7/1986  Jacob ................................. 433/220

*Primary Examiner*—Robert Peshock
*Attorney, Agent, or Firm*—William Nitkin

[57] ABSTRACT

A dental post and method of treatment wherein the tooth is provided with an aperture extending from its root canal to the exterior of the tooth beneath the gum line and a dental post is inserted within the root canal, such post having a plurality of chambers interconnected by at least one channel forming a circulation loop for blood flow between the root canal, through the channel and chambers to the exterior of the tooth through said aperture in the tooth beneath the gum line and back which circulation loop promotes the natural healing of the tooth.

10 Claims, 1 Drawing Sheet

ENDODONTIC POST AND METHOD OF TREATMENT

BACKGROUND OF THE INVENTION

1. Field of the Invention

This invention resides in the field of dental treatment and more particularly relates to a endodontic post and method of use for treatment of teeth requiring crowns or other endodontic procedures.

2. Description of the Prior Art

The use of dental posts for helping to attach an artificial crown to a tooth as well as in root canal therapy is well known in the art. Such posts often have a threaded bottom for screwing securely into the dentine in the tooth's root canal. The threads of such posts engage tightly in the dentine leaving no space between the post and the tooth. The post, usually covered with cement, creates a full contact of the entire post within the root canal of the tooth. Some dental posts have a vertically oriented channel or channels therein to allow for the escape of cement which passes upwards in such channel(s) to allow for the affixation of the post within the tooth. On top of the prepared ground-down tooth and protruding post is usually cemented an artificial crown which is anchored in place by the post.

It is also known in the prior art to form shallow apertures in the sides of teeth for the attachment of various devices thereto such as in orthodontics. Some treatments in root canal therapy involve cutting through the root of the tooth, such as an apicoectomy procedure. U.S. Pat. No. 3,487,544 to Weissman discloses a venting aperture and pin provided in an arificial crown through which excess cement and air can pass to allow for void-free setting of such crown. Such aperture, though, is sealed by the escaping cement. U.S. Pat. No. 275,626 of 1883 to Foss suggests an "education tube" which is a hole extending from the root of the tooth to its exterior above the gum line for drainage which hole can be plugged or unplugged as desired.

In the prior art a tooth may be successfully crowned and later the sealed-over root canal area may become infected or decayed, requiring further treatment including root canal therapy.

SUMMARY OF THE INVENTION

It is an object of this invention to provide a new method of treatment of teeth requiring artificial crowns. The method of this invention, as described in further detail below, involves the creation of a diagonal aperture extending from the root canal area to the exterior of the tooth beneath the gum line which aperture remains open. A post of special design is utilized with this new method which post has on its lower portion a plurality of chambers therearound interconnected by channels which allow fluid to communicate therethrough. When the post is inserted into the root canal area of the rooth, a circulation loop of blood flow is created from the root canal area through such channels and chambers to the aperture in the tooth and therethrough to the exterior of the tooth beneath the gum line. When the artificial crown is cemented in position on the upper portion of the post, the aperture in the tooth and post of this invention allow for a continuous circulation loop of blood from the root of the tooth through the root canal, through the channels and chambers of the post to the gum and also then back into the tooth which circulation helps the root canal area of the tooth to stay alive and heal. The method and post of this invention can in some cases be used in place of traditional root canal therapy.

DESCRIPTION OF THE PREFERRED EMBODIMENT(S)

Figure 1:
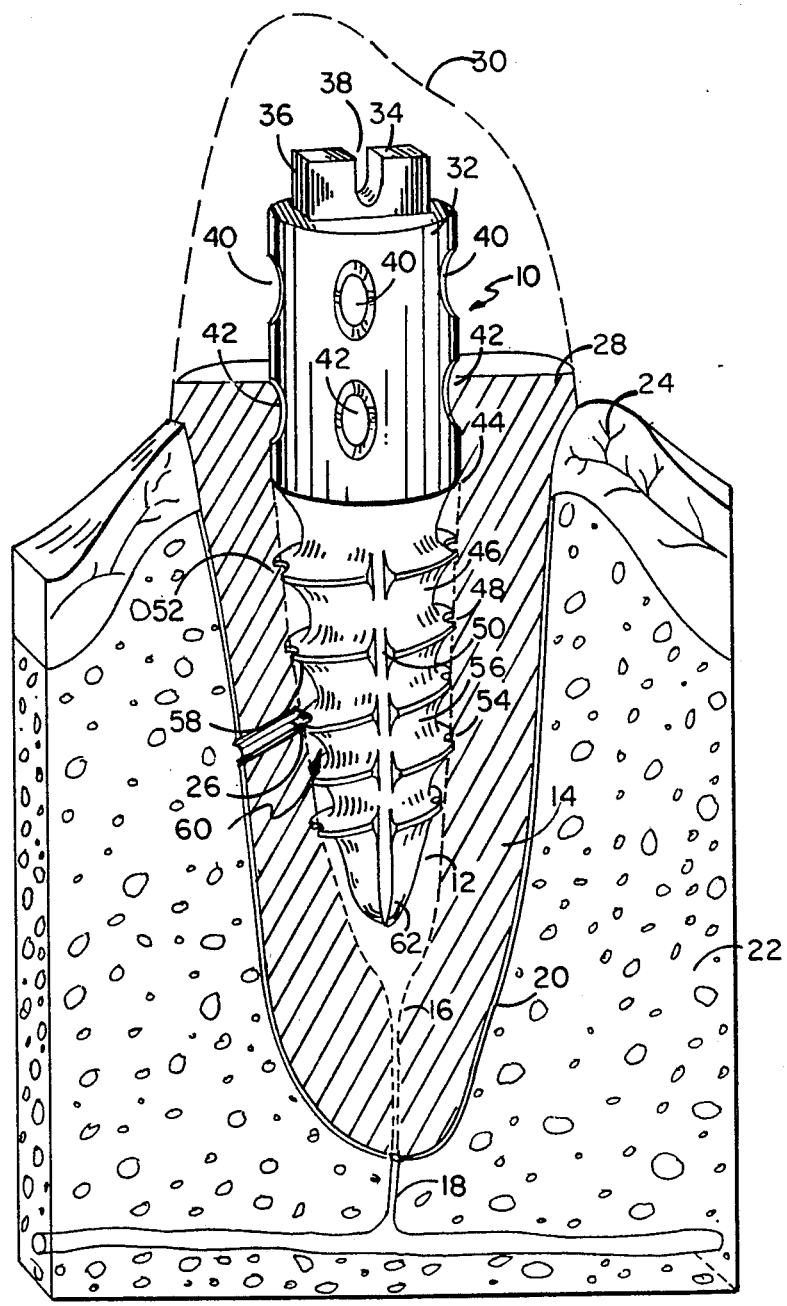
FIG. 1 illustrates a cross-sectional view of a tooth wherein the method of this invention is utilized with the post of this invention.

FIG. 1 illustrates a cross-sectional view of a tooth with post 10 inserted within reamed hole 12 in root canal 16 of the tooth. Crown 30 of the tooth is seen in outline form as it is artificial and is attached above top 28 of remaining tooth body 14. The natural crown has been ground down by normal dental procedures. Remaining tooth 14 is held in bone 22 above which bone is gum tissue 24. Around tooth 14 is periodontal ligament 20. Aperture 26 is drilled diagonally from the root canal area to the exterior of the tooth below the gumline to allow blood circulation from the root canal area through aperture 26 to the exterior of the tooth and back when post 10 is in place. Aperture 26 can be approximately 0.5 mm-1 mm in diameter. It is this circulation of blood that helps promote healing of the tooth. Bone growth will be promoted and such bone will slowly reform in the tooth and around the post.

In order to allow such circulation while the post is in place, the post must be of the specific design as described below. Post 10 has a lower portion below shoulder 44 which is comprised of a plurality of projection threads such as threads 48 and 58 which extend around the post. These projections can be in the form of spiral threads or can be parallel projections threads extending around post 10 and not joining with one another in a continuous spiral. Such threads are disposed at a slight angle so the ends of the threads can be engaged against the sides of the tooth in the soft dentine by a slight rotation, such as 1/20th of a complete rotation, of post 10. This slight rotation will lock the post within reamed hole 12 in root canal 16 of the tooth and will hold it in place. The post does not have to be held in place extremely tightly as do some of the posts of the prior art because as the healing process progresses, bone growth around the post will retain it securely in place. Also it is important that the threads not bite too deeply into the dentine as the areas between the threads form chambers and must be left empty for blood circulation therethrough and these chambers should not contact the dentine which would otherwise fill up the area between the threads in prior art posts and prevent the desired and necessary blood circulation loop of this invention. Between the higher outermost thread portions such as threads 48 and 54 are valley areas such as valley areas 46 and 56 which areas form the plurality of chambers, such as chamber 60, around the post which remains empty of tooth dentine as only the outer edge of the thread engages and bites into the tooth structure. Connecting these chambers and extending to the rounded tip of the post are one or more channels, such as channels 50 and 52, which are seen in this view extending generally vertically and perpendicularly to the direction of the chambers. In one embodiment there can be four channels, each positioned at 90 degrees from one another around post 10. The bottom of the channels is generally at the same depth as the bottom of the chambers which arrangement helps to allow any fluid in one chamber to flow easily through such channels so that such fluids can pass from chamber to chamber through the channels and eventually pass in the channel(s) to rounded end 62 of post 10 into root canal area 16. The thread portions, such as thread portions 58, are thin at their exterior peripheries and extend downward toward the base of the chambers sharply to form relatively deep chambers and also so that in case a thread portion happens to be positioned in front of aperture 26, it will be so thin as to only cover a portion of it, and fluid can pass above and below the thread portion engaged against the opening of aperture 26 and in and out of said aperture.

It should be noted that while channels are frequently seen on posts in the prior art, they are not utilized for the purpose of circulation of blood as disclosed herein but serve to allow the cement in the root canal to escape therethrough and remain plugged with said cement thereafter. The threads in the prior art posts do not take the special form of the threads of this invention and such prior art threads are needed only to retain such posts in position and are filled by the cement and soft dentine when the post is screwed into the root canal. Thus the prior art posts are not used to allow circulation of blood as does the post of this invention. In this device it is expected that any cement used will not go below shoulder 44 since one does not wish to have any cement within the chambers or channels in the lower portion of the post of this invention. At shoulder 44 a small amount of cement can be utilized to help retain it in place and to seal the root canal chamber from the new artificial crown to be inserted on upper portion 32 of post 10. The upper portion of post 10 has defined on its surface a plurality of concave dimples such as concave dimples 40 and 42, which help the crown to be held thereon by cement solidifying in said concave dimples in its normal fashion. Pairs of concave dimples, one above the other, can be provided at positions 90 degrees to one another around the post, but it should be noted that other retention configurations can be utilized. Further, slot 38 for receipt of a rotation tool can be provided in top 34 of post 10. Top 34 can also be squared off in a configuration to be installed by a small square-ended wrench for better control when rotating post 10 gently in the reamed root canal hole 12 of the tooth.

The post material can be titanium or gold which are both conventional materials for dental posts. The dimensions of the post of this invention can be approximately 1.5 cm-2 cm in length with the bottom portion of the post being at least 0.5 cm long and the upper portion extending from approximately 1 cm-1.5 cm above the area of the tooth's root system onto which upper portion the artificial crown is cemented. The threads can have a depth of approximately 0.5 mm-1 mm, and the chambers can have a width of approximately 1 mm.

It should be noted that teeth treated with the endodontic post and method of my invention will heal which healing process is often unnecessarily eliminated in traditional root canal therapy by the removal of the root and surrounding pulp. The lower portion of the tooth will be nourished by the circulation provided in my method during the healing process and natural functions will eventually aid and take over the circulatory function of the aperture drilled in the side of the tooth as teeth naturally have minute channels and blood vessels in them which will eventually start to operate in the healed tooth.

Although the present invention has been described with reference to particular embodiments, it will be apparent to those skilled in the art that variations and modifications can be substituted therefor without departing from the principles and spirit of the invention.

I claim:

1. A dental post able to provide blood circulation within a tooth after insertion of the post into the root canal area of a tooth, said dental post comprising:
   an upper post portion for support of an artificial crown;
   a lower post portion for uncemented insertion into the root canal area of a tooth;
   a plurality of projection threads extending from said lower post portion for uncemented engagement with the sides of a tooth;
   a plurality of blood circulation valley areas between said projection threads on said lower post portion, said valley areas forming a plurality of empty chambers for the circulation of blood after said projection threads have engaged the sides of a tooth; and
   at least one empty channel for blood circulation extending generally perpendicular to and intersecting said valley areas on said lower post portion, said empty channel providing circulation of blood between said chambers after uncemented insertion of said lower post portion into a tooth.

2. The dental post as recited in claim 1 wherein a plurality of said empty channels are disposed on said lower post portion.

3. The dental post as recited in claim 2 wherein four empty channels are disposed at 90° to one another on said lower post portion.

4. The dental post as recited in claim 1 further comprising means to assist in retaining an artificial crown on said upper post portion.

5. The dental post as recited in claim 4 wherein said means to assist in retaining said artificial crown comprises a plurality of concave dimples defined in said upper post portion.

6. The dental post as recited in claim 5 further comprising rotation device engagement means including a slot disposed in said upper post portion and wherein said upper post portion is formed as a rectangle.

7. A dental crown structure able to provide blood circulation within a ground down tooth, said dental crown structure comprising:
   a reamed hole in the root canal area of a ground down tooth;
   an aperture in the tooth extending from said reamed hole to the exterior of the tooth below the gum line;
   a dental post inserted in said reamed hole, said dental post being comprised of:
      an upper post portion for support of an artificial crown,
      a lower post portion for uncemented insertion into said reamed hole,
      a plurality of projection threads extending from said lower post portion which engage the sides of said reamed hole,
      a plurality of empty chambers for blood circulation on said lower post portion between said engaged projection threads,
      at least one empty channel for blood circulation extending generally perpendicular to and intersecting said empty chambers on said lower post portion; and an artificial crown anchored to said upper post portion of said inserted dental post.

8. A method for dental treatment of a tooth requiring an artificial crown wherein the upper portion of the tooth has been ground down, said method comprising the steps of:

providing a dental post in the root canal area of the tooth, said dental post being comprised of:

an upper post portion for support of an artificial crown, a lower post portion inserted without cement into the root canal area of a tooth, a plurality of projection threads engaging the tooth, a plurality of empty chambers for blood circulation on said lower post portion between said engaged projection threads, and at least one empty channel for blood circulation generally perpendicular to and intersecting said chambers on said lower post portion;

forming a circulation loop for blood flow between the root canal of the tooth by said dental post to the exterior of the tooth at a point under the gum line; and anchoring an artificial crown on said upper post portion of said dental post.

9. The method as recited in claim 8 further comprising the step of drilling an aperture extending from the root canal to the exterior of the tooth at a point beneath the gum line prior to providing said dental post.

10. The method as recited in claim 8 or 9 further comprising the steps of:

reaming a dental post receipt hole in the root canal area; and inserting said dental post in said reamed receipt hole.

* * * * *